United States Patent [19]
Vaughan

[11] 4,317,949
[45] Mar. 2, 1982

[54] ALKYLATION PROCESS AND APPARATUS USEFUL THEREIN

[75] Inventor: Ronald J. Vaughan, Claremont, Calif.

[73] Assignee: Varen Technology, Marshallton, Del.

[21] Appl. No.: 660,634

[22] Filed: Feb. 23, 1976

[51] Int. Cl.$^3$ .......................... C07C 2/66; C07C 2/70
[52] U.S. Cl. .................................. 585/458; 568/607
[58] Field of Search .......... 260/671 C, 671 B, 671 R, 260/683.47, 683.58, 543 F; 585/458

[56] References Cited

U.S. PATENT DOCUMENTS

| | | | |
|---|---|---|---|
| 2,843,642 | 7/1958 | Kelly | 260/671 C |
| 2,971,992 | 2/1961 | Bloch | 260/671 R |
| 3,037,052 | 5/1962 | Bortnick | 260/671 R |
| 3,116,346 | 12/1963 | Van Dyke | 260/671 R |
| 3,239,575 | 3/1966 | Frilette et al. | 260/671 R |
| 3,624,053 | 11/1971 | Gibbs et al. | 260/543 F |
| 3,894,090 | 7/1975 | Cleveland | 260/671 R |
| 3,960,764 | 6/1976 | Bernard et al. | 260/683.47 |

FOREIGN PATENT DOCUMENTS

733753  7/1955  United Kingdom ............ 260/671 C

*Primary Examiner*—Curtis R. Davis
*Attorney, Agent, or Firm*—Charles J. Tonkin

[57] ABSTRACT

This invention relates to conversion processes which take place in the presence of solid acid catalysts, e.g., hydrocarbon conversion processes. More specifically, this invention relates to a process for the alkylation of organic compounds, preferably aromatic and paraffinic hydrocarbons, with alkylating agents, e.g., alkyl chlorides, alkyl sulfonates, alkyl epoxides, alkynes, etc., in the presence of a polyfluorosulfonic acid catalyst. In one preferred embodiment of the instant process the selectivity to the monoalkylated reaction product of said organic compound and said alkylating agent is maximized by (1) refluxing a mixture comprising said compound and the alkylated derivative thereof, (2) separating from the mixture of step (1) an overhead product comprising said organic compound, said overhead product being substantially free from said alkylated derivatives, (3) condensing said overhead product, (4) contacting said condensed overhead product with said alkylating agent in the presence of a polyfluorosulfonic acid catalyst, at conditions whereby a portion of said organic compound is reacted to form the alkylated derivative thereof, and (5) returning the resultant mixture of the organic compound and its alkylated derivative to the refluxing mixture of step (1). Fresh organic compound may be continuously added to said refluxing mixture while continuously withdrawing said alkylated derivatives. Preferably said organic compound is benzene and said olefin is selected from the group consisting of ethylene and propylene.

3 Claims, 1 Drawing Figure

ALKYLATION PROCESS AND APPARATUS USEFUL THEREIN

FIELD OF THE INVENTION

Figure 1:
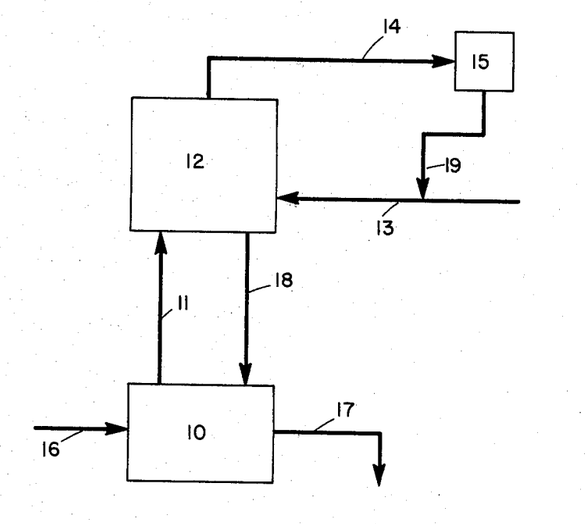

This invention relates to conversion processes which take place in the presence of solid acid catalysts, e.g., hydrocarbon conversion processes. More specifically, this invention relates to a process for the alkylation of organic compounds, preferably aromatic and paraffinic hydrocarbons, with alkylating agents, e.g., alkyl chlorides, alkyl sulfonates, alkyl epoxides, alkynes, etc., in the presence of a polyfluorosulfonic acid catalyst. In one preferred embodiment of the instant process the selectivity to the monoalkylated reaction product of said organic compound and said alkylating agent is maximized by (1) refluxing a mixture comprising said compound and the alkylated derivative thereof, (2) separating from the mixture of step (1) an overhead product comprising said organic compound, said overhead product being substantially free from said alkylated derivatives, (3) condensing said overhead product, (4) contacting said condensed overhead product with said alkylating agent in the presence of a polyfluorosulfonic acid catalyst, at conditions whereby a portion of said organic compound is reacted to form the alkylated derivative thereof, and (5) returning the resultant mixture of the organic compound and its alkylated derivative to the refluxing mixture of step (1). Fresh organic compound may be continuously added to said refluxing mixture while continuously withdrawing said alkylated derivatives. Preferably said organic compound is benzene and said olefin is selected from the group consisting of ethylene and propylene.

BACKGROUND OF THE INVENTION

Alkylation refers generally to the addition of an alkyl group to an organic compound. One well-known alkylating agent useful in the preparation of a wide variety of alkylated derivatives is the olefin. For example, "isooctane," a high octane number petroleum fraction, which is valuable as a fuel may be prepared by the alkylation of isobutane and 2-butene. Other similarly highly branched hydrocarbons may be prepared in an analogous manner by varying the olefin and the isobutane reactants. This specific alkylation process may be carried out thermally or in the presence of an acid catalyst, such as hydrogen fluoride or sulfuric acid. The thermal alkylation process is not generally used because of the high temperatures required and the undesired distribution of products resulting from the thermal alkylation.

The acid catalyzed alkylation process is subject to various difficulties also, one very important one being recovery of the spent acid from the alkylated product.

In the acid catalyzed alkylation process, the ratio of isobutane to olefin must be maintained at a high level and the heat of reaction quickly dissipated to minimize the formation of olefin polymers and/or alkylated products comprising more than one added olefin unit.

Alkylation processes are also used to prepare various useful alkylated derivatives of benzene and naphthalene. For example, dodecylbenzene, a useful precursor for the surfactant industry may be prepared by the alkylation of benzene with dodecene in the presence of an aluminum chloride catalyst. The aluminum chloride catalyst continuously deactivates and forms a sludge which is recovered and regenerated only at great cost and difficulty. In all of these processes a solid catalyst which is easily separated from the reaction mixture is desirable.

Other examples of commercially important alkylation processes include the alkylation of benzene with ethylene or propylene to yield ethylbenzene, which may be subsequently converted to styrene; and cumene, which may be subsequently converted to phenol and acetone, respectively. Catalysts useful in these processes include phosphoric acid supported on kieselguhr and aluminum chloride. In each of the above benzene alkylation processes the tendency to form polyalkylated derivatives, as impurities, is a noted problem.

In U.S. Pat. Nos. 3,037,052; 3,017,441; and 3,239,575, the use of various forms of sulfonated polystyrene as a catalyst for alkylation processes is disclosed. The difficulties of using sulfonated polystyrene include (1) cleaning residual organic "tars" from the catalyst; (2) gradual changes in the catalyst properties due to the alkylation of unsulfonated styrene residues; and (3) physical fragility of highly sulfonated styrene-divinyl benzene copolymers. In all of these patents, there is no mention of the use of polyfluorosulfonic acid polymers as catalysts for the alkylation processes described therein.

SUMMARY OF THE INSTANT INVENTION

The instant invention relates to a conversion process which is carried out in the presence of a solid acid catalyst, e.g., a hydrocarbon conversion process. In one embodiment, the process of the instant invention relates to the alkylation of an organic compound with an olefin and comprises the step of contacting said compound and said olefin at reaction conditions in the presence of a polyfluorosulfonic acid catalyst. Preferably, the organic compound is a hydrocarbon and the olefin is a $C_2$ to $C_{20}$ olefinic material, most preferably an alpha olefin.

The hydrocarbon reactant may be an aromatic or a paraffinic material depending on the desired reaction product. In one aspect of the invention, the preparation of the alkylated derivatives of benzene is contemplated. In this embodiment, the hydrocarbon is benzene and the olefinic reactant is selected from the group consisting of $C_2$ to $C_{20}$ olefins, especially alpha olefins. For example, when the desired reaction product is ethylbenzene, the olefin is ethylene, while when the desired reaction product is isopropylbenzene, propylene is used as the olefin. One commercially desirable reaction product is dodecylbenzene which is useful in the preparation of synthetic detergents. This alkylated product is prepared by the reaction of dodecene and benzene.

In another embodiment of the instant invention, alkylated products useful as motor fuels are desired. In this embodiment, the hydrocarbon is generally a $C_4$ to $C_6$ alkane having an iso structure, i.e. a hydrocarbon having at least one tertiary carbon, e.g., 2-methylpropane and 2-methylbutane, 2-methylpentane. In this embodiment of the instant invention the olefin may be ethylene, propylene or isobutene since it is desired that the alkylate fraction useful as a fuel has no more than about 10 carbon atoms.

In general, the olefins which are useful as alkylating agents in the process of the instant invention include ethylene, propylene, 1-butene, 2-butene, 2-methyl-1-butene, 1-hexene, 2-methyl-1-hexene, 1-heptene, 3-heptene, 4-octene, 2-decene, 3-methyl-1-decene, 4-ethyl-1-decene, dodecene, 2-methylpropene, etc.

Compounds which may be alkylated by means of the process of the instant invention include (1) mono- and polynuclear aromatics, including condensed ring aromatics, having from 6 to 20, preferably 6 to 10 carbon atoms, e.g., benzene, naphthalene, biphenyl, and various alkyl, hydroxy, carboxy, halogen substituted derivatives thereof, providing, however, that at least one site is available which is capable of combination with the alkylating agent, e.g., phenol, methoxybenzene, toluene, or the meta and paraxylene, chlorobenzene, etc.; (2) paraffins, including straight and branched chains, e.g., $C_4$ to $C_{10}$ paraffins, preferably $C_4$ to $C_6$ isoparaffins; and (3) organic acids, i.e. saturated or unsaturated carboxylic acids may be used and with the exception of oxalic acid, which is operable, are of the general formula $$R(COOH)_z$$

in which R is selected from the group consisting of hydrogen, carboxyl, a hydrocarbon group, and $$CH_2=C- \atop | \atop H(CH_2)_n$$

in which n is an integer from 0 to 2 and z is an integer from 1 to 2; typical examples of the acids include formic, acetic, propionic, butyric, isobutyric, valeric, caprylic, pelargonic, lauric, myristic, palmitic, stearic, pivalic, triethylacetic, diproplyacetic, neopentylacetic, neopentyldimethylacetic, oxalic, malonic, succinic, glutaric, adipic, pimelic, sebacic, acrylic, methacrylic crotonic, angelic, tiglic, undecylenic, oleic, cyclohexanecarboxylic, pinonic, cyclopropanecarboxylic, benzoic, toluic, mesitylic, durylic, α-naphthoic, β-naphthoic, phenylacetic, p-tolylpropionic, β-naphthylacetic, p-chlorobenzoic, m-methoxyphenylacetic, piperonlyic, veratric, phthalic, isophthalic, terephthalic, naphthalic, m-bromobenzoic, homoveratric, cinnamic, dihydrocinnamic, octahydrocinnamic, tetrahydrobenzoic, endomethylenetetrahydrobenzoic, methoxyacetic, ethoxypropionic, butoxybutyric, phenoxyacetic, 2,4-dichlorophenoxyacetic, 2,4,5-trichlorophenoxyacetic, cyanoacetic, chloroacetic, α,α-dichloropropionic, α,β,β-trichloroacrylic trichlorocrotonic, dichloroacetic, α-bromopropionic, trimesic, fumaric, maleic, itaconic, citraconic, aconitic, muconic and acetylenedicarboxylic acids; and (4) water and alcohols, e.g., ethanol, isopropanol, butanol, etc., i.e. of the general formula $$R_1-(OH)_y$$

wherein $R_1$ is a hydrocarbyl radical or hydrogen, or oxygenated derivative thereof, e.g., an alkylene oxide radical, preferably a $C_1$ to $C_{10}$ alkyl or alkylene radical and y is an integer of 1 or 2 respectively.

The products formed by alkylation of the above compounds are (1) alkyl aromatics, (2) higher carbon number paraffins, (3) esters, and (4) diols and ethers respectively.

The polyfluorosulfonic acid catalyst which is used in the process of the instant invention is a fluorocarbon polymer containing pendant sulfonic acid and may be derived from fluorocarbon polymers having mixed chlorine and fluorine substituents, wherein the number of chlorine atoms is not more than about 20% of the total chlorine and fluorine atoms present in said polymer. The perfluorinated derivatives of these materials are particularly useful in the process of the instant invention and said perfluorocarbon polymer may have the pendant sulfonic acid attached either directly to the main polymer chain or to perfluorocarbon side chains which are attached to the main polymer chain. Either or both of the main polymer chain and the side chain may contain oxygen atom linkages, such as ether linkages, for example, as in Nafion, perfluorosulfonic acid membrane obtained from E. I. duPont de Nemours and Company. The perfluorocarbon polymer particularly useful in the present invention may be prepared as disclosed in U.S. Pat. Nos. 3,041,317; 3,282,875; and 3,624,053, hereby incorporated by reference. The most preferred polymers are prepared by copolymerizing a perfluorovinyl ether having the formula:

$$FSO_2CF_2OCF(CF_3)CF_2OCF=CF_2$$

and tetrafluoroethylene followed by conversion of the $SO_2F$ group to a sulfonic acid group. The equivalent weight of the preferred copolymer preferably ranges from 850 to 2500 where the equivalent weight is defined as the average molecular weight per sulfonyl group.

The catalyst may be used in the process of the instant invention in various physical forms, that is it may be fabricated into sheets, hollow tubes, granules having a particle size of from 6 mesh to less than 400 mesh, fibers, etc. The catalyst may be used in a supported or unsupported manner, e.g., the catalyst can be coated onto a metal having good heat exchanger properties, as further described below. It is important to note that the catalyst of the instant invention is insoluble in, and inert to deactivation by the various reactant mixtures, at the conditions at which the alkylating process is carried out, thus providing ease of separation and longer catalyst life than the various solid and liquid catalysts used in the prior art, such as sulfonated polystyrene, sulfuric acid, HF, and phosphoric acid supported on kieselguhr.

A critical preparation of the polyfluorosulfonic acid catalyst for use in the alkylation process of the instant invention is necessary. It has been found that the polyfluorosulfonic acid, that has not been treated as described below, is much less active in catalyzing the alkylation process. However, an active catalyst is conveniently obtained by means of a process which comprises the sequential steps of (1) contacting polyfluorosulfonic acid with a strong acid (pKa less than zero) at elevated temperatures, e.g., 70% nitric acid at a temperature of about 110° C., (2) contacting said acid treated polyfluorosulfonic acid of step (1) with distilled water for a time sufficient to remove soluble, residual acid, and (3) drying the polyfluorosulfonic acid of step (2) by contacting with a dry, inert gas, for example, nitrogen containing less than 10 ppm water at a temperature of at least 120°, more preferably from 140° to 180° C. for a time of at least 2 hours, more preferably for from about 4 to about 6 hours. Alternatively, step (3) can be carried out by drying the polyfluorosulfonic acid of step (2) by heating under vacuum at temperatures of from 140° to 180° C. for a period of at least two hours.

The catalyst may be cleaned after use in the same manner, that is it has been found that when running the process of the instant invention at high temperatures the catalyst tends to darken and lose some activity. It is noted that although the catalyst appears blackened it is still active for carrying out the alkylation process. However, the catalyst may be conveniently cleaned by means of the above-described technique. The catalyst may be cleaned batchwise or, alternatively, the catalyst may be continuously separated from the various reactant and reactant products and cleaned prior to recycling to the reaction.

In the process of the instant invention, the organic compound which is to be alkylated is contacted with an olefin in the presence of the above-described catalysts. The temperature and pressures are maintained to maximize the formation of the desired product, usually the monoalkylate. The ratios of olefin and organic compound are varied to ensure that only a very small amount of polymerization product is obtained, for example, the ratio of the organic compound to the olefin is preferably held at a level of from 2 to 1, more preferably from 10 to 1 to ensure that the olefin will not self react to form a polymeric product or react further with the monoalkylation product. The adjustment of temperature and pressures to obtain the desired high polyalkylated product would be also obvious to the skilled artisan. For example, temperatures of from 0° C. to 200° C. and pressures of from 0 psig to 1000 psig may be conveniently used although the specific operating pressures will relate to the specific organic compounds and olefins which are to be used. In general, the pressure is adjusted so as to keep the organic compound in the liquid phase at the catalyst operating temperature. The temperature is chosen so as to provide a convenient conversion rate while minimizing tar formation on the catalyst. The olefin and organic compound feed rates are adjusted so as to provide substantially complete conversion in the time of passage through the catalyst zone, as evidenced by a lack of olefin in the reactor effluent.

The presence of moisture and other impurities should be avoided in carrying out the process of alkylation. Basic materials should also be excluded from contact with the reactants and the catalyst during the alkylation reaction. For example, amines, inorganic bases, e.g., NaOH, sulfur compounds, for example $CH_3SH$, $CH_3-S-S-CH_3$ should be carefully excluded. The skilled artisan will especially appreciate that no more than 0.05 wt. % water, preferably no more than 0.01 wt. % water, should be present in the reactant feed streams.

In the specific examples given above, that is the alkylation of benzene to form plastic and surfactant precursors and the alkylation of isoparaffins to yield motor fuels, the following reaction parameters may be conveniently used: benzene may be contacted with ethylene at a temperature of from 50° to 190° C. and a pressure of from 0 psig to 150 psig. The ratio of benzene to ethylene is kept at a level of from 10 to 3 to maximize the formation of the monoalkylated product. When propylene is substituted for ethylene, the temperature and pressures may vary from 30° to 190° C. and 0 to 100 psig, respectively. The ratio of benzene to propylene will be maintained at 10 to 3. Since propylene is more reactive as an alkylating agent than ethylene, the ratio of benzene to propylene should be kept higher.

In the preparation of a motor fuel by the process of the instant invention, isobutane is contacted with ethylene or propylene, at a temperature of from 0° C. to 150° C. and a pressure of from 50 to 1000 psig. The ratio of the isobutane to olefin is kept at least 1, more preferably 5 to 20 to maximize the formation of monoalkylates and to minimize the polymerization products which are of low octane value.

It will thus be apparent from the above specific example that it is very desirable to maximize the formation of the monoalkylate product. In one much preferred mode of operating the process of the instant invention, which is described in the attached figure, a mixture of the organic compound which is to be alkylated and various alkylated derivatives thereof are refluxed in zone 10. An overhead product comprising the organic compound, said product being substantially free of the alkylated derivatives is separated from the mixture and led through conduit 11 into zone 12 wherein it is condensed. The alkylating olefin is brought into zone 12 through line 13 and contacted therein with the condensed overhead product in the presence of the catalyst of the instant invention. Conditions are maintained in zone 12 sufficient to convert at least a portion of the organic compound present in said condensed overhead product to the monoalkyl derivative thereof. The monoalkyl derivative may be returned via conduit 18 along with the unconverted organic compound to zone 10. The unreacted olefin is passed through conduit 14 into zone 15 wherein it may be recovered and recycled via conduit 19 to zone 12. In one preferred embodiment of the process of the instant invention, fresh organic compound is continuously added through line 16 to zone 10 while a fraction containing a substantially high amount of the alkylated derivatives of said organic compound is withdrawn through conduit 17. When operating in this manner, the following advantages are obtained. An organic compound essentially free of its higher boiling alkylated derivatives is continuously contacted with the olefinic stream in zone 12. Thus, the selectivity to the monoalkylated product is increased. Furthermore, the heat of the alkylation reaction is used to provide the refluxing of the mixture in zone 10, thus heating economy is obtained.

The above-described preferred mode of operating the process of the instant invention is not limited to carrying out alkylation reactions, nor is it limited only to the preferred catalysts of the instant invention, that is the polyfluorosulfonic acid. The preferred mode, in general, is applicable to any process wherein it is desirable to minimize the sequential reaction of a reactant to form undesirable products, that is in any reaction wherein a first reactant combines with a second reactant to form a reaction product which may subsequently react with said second reactant to give undesirable impurities. The preferred mode of operation is especially suitable in instances wherein the reaction product will further react with the second reactant at a greater rate than the first reactant. The selectivity to the reaction product may be improved by means of the process of the instant invention. Of course, in this scheme the reaction product must have a higher boiling point than the first reactant. Furthermore, the second reactant preferably has a much lower boiling point (preferably greater than 20°) than either said first reactant or said reaction product, i.e., so that it will not be returned in its unreacted form to the refluxing mixture exemplified in zone 10 of the instant invention. In general, any difference in boiling point of, for example, at least 5° C. between the reaction product and the first reactant is suitable for carrying out the process in this preferred mode. Preferably, the reaction product will have a boiling point at least 10° C. greater than the boiling point of the first reactant.

It is noted that the skilled artisan may make various variations on this preferred mode of operation, all of which are within the spirit of the instant invention. For example, the first reactant may be condensed in the same zone in which the solid acid catalyst is contained or may be condensed in a tower at a point located above the solid acid catalyst and fed by gravity to the catalyst zone. The reaction which takes place in the presence of a catalyst can be either a liquid or gas phase reaction since examples of each will be readily apparent to the skilled artisan. Finally, the catalyst can be any solid material having the requisite catalytic activity. For example, in the alkylation process described above, the polyfluorosulfonic acid may be substituted with the sulfonated polystyrene catalysts of the art although it is much preferred to use the polyfluorosulfonic acid catalyst for the reasons already noted.

One important example of carrying out a well-known process in the preferred mode of operating the process of the instant invention is the chlorination in the presence of a Lewis acid, e.g., $FeCl_3$, of organic compounds, for example, benzene and toluene at the various ring positions. Operating in this manner, the purely monosubstituted derivatives of benzene and toluene, for example, monochlorobenzene or monochlorotoluene (a mixture of ortho and parachlorotoluene isomers) may be obtained.

Other reactor designs to carry out the process of the instant invention will be well known to the skilled artisan. Some specific reactor designs are described hereinbelow.

As stated above, the process of the instant invention also relates to hydrocarbon conversion processes other than alkylation. For example, it has been found that isomerization, which may be considered as an intramolecular alkylation as opposed to the intermolecular alkylation process described above, may be conveniently carried out in the presence of the above-described polyfluorosulfonic acid catalyst. For example, a mixture of the isomers of xylene may be isomerized into a fraction having different ortho, meta, para distribution than the starting mixture. Another process contemplated in the instant invention is the dealkylation of alkyl benzenes. For example, a mixture comprising either diisopropyl benzene or diethyl benzene and benzene may be converted to the monoalkylated benzene in the presence of the polyfluorosulfonic acid catalyst described above. Other examples of suitable hydrocarbon conversion processes will be known to the skilled artisan.

SPECIFIC EMBODIMENTS

Four reactor configurations were utilized for the alkylation reactions:

Reactor #1:

A stainless steel tube (304 SS, 35"×¼" O.D.×0.200" I.D.) packed tightly with Nafion fiber (1200 equivalent weight (E.W.); 18.8 g, <0.001 diameter) and fitted with tube fittings on each end.

Reactor #2:

A stainless steel tube (304 SS, 34"×¼" O.D.×0.200" I.D.) surrounding a tightly-packed bundle of parallel tubular Nafion TM membranes, 1200 E.W., each 0.024" I.D.×0.036" O.D.) cut flush with the ends of the stainless steel jacket tube. The total weight of the membrane material was 9.32 g.

Reactor #3:

A FEP-Teflon TM tube, (112"×¼" O.D.×0.186" I.D.) filled with granular Nafion resin (57–60 g, 1200 E.W., screened 20/40 mesh) and fitted with glass wool plugs and reducing unions on each end.

The above reactors were mounted in a forced-fan oven controlled to ±0.5° C. Check valves were placed on the exit of the reactor to provide back pressure in the system. Olefin and benzene were mixed (as two phases) in a "cross" at the entrance of the reactor; the fourth arm of the cross was connected to a pressure gauge.

Olefin flow was monitored by a small "rotometer" calibrated for each gas used over a range of pressures encompassing the actual pressures used. Benzene flow was provided either from a calibrated syringe pump or from a metering pump. Samples were collected from the reactor exit into 18×150 mm test tubes and quickly sealed before analysis.

Reactor #4: "Recycling Reactor" (the preferred mode described above)

A boiling flask (500 ml, with side arm) was fitted (in ascending order) with (1) a vacuum-jacketed fractionating column (2 cm I.D.×29 cm) filled with stainless steel helice packing, (2) a short connecting tube with a side arm for introduction of gaseous olefin, (3) a reflux condenser with Nafion TM fiber packed into the inner tube of the condenser and vacuum applied to the annular jacket, (4) a water-cooled reflux condenser, (5) a bubbler filled with fluorocarbon oil, for monitoring exit gas, (5) a drying tube connecting to the atmosphere.

To initiate reaction, benzene was refluxed through the system to the upper condenser; then olefin was introduced through the gas inlet. Samples were periodically withdrawn from the pot with a syringe and analyzed by gas chromatography.

Nafion TM perfluorosulfonic acid resin was obtained from duPont, Wilmington, Delaware. Weights of resin are those before any processing, i.e. equilibrated with atmospheric humidity. After packing the resin into the reactor, it was prepared for use by successive passage of (1) 70% nitric acid at 110° C., (2) distilled water, and (3) dry nitrogen at 140°–160° for 4–6 hours. The last step is critical to the activity of the resin as a catalyst in removing the water of hydration.

Benzene was dried by distillation through a helice packed column from phosphorus pentoxide, prior to use.

EXAMPLE 1

Reaction of Ethylene with Benzene

Concomitant flow of a two-phase mixture of benzene and ethylene through a tubular reactor packed with Nafion TM polymer (tube bundle, fiber, or granular form) led to efficient conversion of the ethylene to ethyl benzene and small amounts of polyethylbenzenes. The effect of increasing both temperature and ethylene flow rate was investigated; the ethylene flow was in general kept higher than the point at which gas was observed in the effluent from the reactor (unreacted ethylene). This led to relatively poor conversion (Table I), due both to the unreacted ethylene and to "channeling" of gas flow through the reactor. A broad temperature optimum is seen at 80°–90°.

Ethylene flow was increased at constant temperature and benzene flow. Conversion increased until the point at which gas was observed in the outlet, at which point conversion dropped sharply (Table II).

TABLE I

Reaction of Ethylene with Benzene in the Presence of Nafion™
Reactor #1
Benzene Flow 0.28 ml/min

| Sample | T (°C.) | Ethylene Flow (ml/min) | P (psig) | Ethylene mmoles/min | Ethylbenzene (% wt/vol) | Diethylbenzene(s) (% wt/vol) | Triethylbenzenes (% st/vol) |
| --- | --- | --- | --- | --- | --- | --- | --- |
| 2 | 41 | 2 | 33 | 0.6 | 4.5 | 0.27 | — |
| 4 | 52 | 2 | 35 | 0.7 | 2.9 | — | — |
| 6 | 62 | 2 | 35 | 0.7 | 4.0 | 0.2 | — |
| 8 | 73 | 2 | 32 | 0.6 | 15.4 | 2.14 | 0.2 |
| 10 | 83 | 4 | 35 | 1.0 | 18.1 | 3.4 | 0.6 |
| 12 | 83 | 8 | 35 | 1.9 | 21.9 | 4.5 | 1.6 |
| 14 | 82 | 8 | 35 | 1.9 | 17.1 | 3.0 | 0.5 |
| 16 | 92 | 8 | 35 | 1.9 | 19.1 | 6.1 | 2.0 |
| 18 | 102 | 8 | 38 | 2.0 | 13.1 | 4.2 | 1.6 |
| 20 | 110 | 8 | 35 | 1.9 | 13.2 | 3.4 | 1.1 |
| 22 | 120 | 8 | 37 | 2.0 | 14.5 | 4.4 | 1.4 |
| 24 | 132 | 8 | 35 | 1.9 | 18.1 | 10.2 | 3.7 |

8 had all liquid in effluent; otherwise excess ethylene flow in all cases.

TABLE II

Conditions as in Table I, except Benzene Flow 0.17 ml/min, T = 94.5° C.

| Sample | Ethylene Flow (ml/min) | P psig | Ethylene mmoles/min | Ethylbenzene (% wt/vol) | Diethylbenzene (% wt/vol) | Triethylbenzene (% wt/vol) | Comments |
| --- | --- | --- | --- | --- | --- | --- | --- |
| 4 | 0.5 | 32 | 0.15 | 6.1 | 0.3 | — | All liquid |
| 6 | 1.0 | 33 | 0.3 | 12.5 | 1.4 | 0.27 | All liquid |
| 8 | 2 | 35–37 | 0.6 | 21.3 | 3.7 | 0.8 | All liquid |
| 10 | 4 | 32 | 1.0 | 52 | 10.6 | 1.6 | All liquid |
| 12 | 12 | 32 | 2.4 | 13.1 | 2.6 | 0.7 | Mostly gas |
| 14 | 25 | 32 | 4.4 | 6.8 | 1.0 | — | Mostly gas |

Results were essentially the same using a longer tube filled with granular resin (Reactor #3); the transparent FEP Teflon tube enabled visual observation of the ethylene absorption and any channeling. Contact of ethylene with dry Nafion resin with or without the presence of benzene produced an immediate yellow-green coloration of the resin. Both temperature and ethylene flow were increased in this experiment, maintaining the ethylene flow below the point at which significant amounts of gas appeared in the effluent. A broad temperature maximum was again observed, in this case about 95°–105°; above this temperature conversion was essentially constant. Higher temperatures did lead to considerable discoloration of the resin; however, activity for ethyl benzene production continued even after the resin had become entirely black (Table III).

Preparative runs were made with both of the above reactors to test catalyst life and confirm the product identifications.

TABLE III

Reaction of Benzene with Ethylene
Reactor #3: 9' Tube, Granular Nafion Resin (20/40 Mesh)

| Sample | T (°C.) | Ethylene Flow (ml/min) | P (psig) | Ethylene mmoles/min | Benzene ml/min | Ethylbenzene (% wt/vol) | Diethylbenzene(s) (% wt/vol) | Triethylbenzenes (% wt/vol) | Comments |
| --- | --- | --- | --- | --- | --- | --- | --- | --- | --- |
| 3 | 65 | 4 | 32 | 1.0 | 0.30 | 14.8 | — | — | Some vapor |
| 5 | 76 | 4 | 32 | 1.0 | 0.31 | 12.7 | — | — | All liquid |
| 8 | 76 | 4 | 32 | 1.0 | 0.26 | 13.8 | 2.9 | — | All liquid |
| 9 | 85 | 4 | 32 | 1.0 | 0.49 | 15.5 | 2.8 | — | All liquid |
| 12 | 85 | 10 | 35 | 2.2 | 0.48 | 19.8 | 4.6 | — | All liquid |
| 15 | 85 | 20 | 37 | 3.9 | 0.48 | 17.0 | 4.2 | 1.1 | Mostly gas |
| 17 | 95 | 20 | 35 | 3.8 | 0.48 | 23.3 | 8.2 | 2.6 | All liquid |
| 18 | 95 | 20 | 35 | 3.8 | 0.48 | 24.2 | 9.6 | 2.2 | All liquid |
| 20 | 104 | 20 | 37.5 | 3.9 | 0.48 | 23.0 | 8.9 | 2.8 | All liquid |
| 21 | 104 | 20 | 38 | 4.0 | 0.48 | 26.2 | 7.2 | 5.3 | Some gas |
| 25 | 116 | 20 | 40 | 4.1 | 0.62 | 19.2 | 6.3 | 2.4 | Some gas |
| 26 | 116 | 20 | 40 | 4.1 | 0.62 | 17.8 | 5.9 | 2.1 | Some gas |
| 28 | 125 | 20 | 40 | 4.1 | 0.55 | 16.7 | 6.1 | 2.2 | Mostly gas |
| 30 | 135 | 20 | 33 | 3.6 | 0.62 | 18.7 | 6.6 | 1.7 | Mostly gas |
| 32 | 145 | 20 | 33 | 3.6 | 0.62 | 20.3 | 7.3 | 1.0 | Reactor black |

EXAMPLE 2

Ethylbenzene from Ethylene and Benzene using Reactor #3

The reactor was cycled in the usual manner with final drying at 185° for several hours. It was cooled to 95°, fitted with an exit check valve, and filled with benzene. When the reactor was nearly filled, ethylene was added into the inlet flow. Samples of the effluent were analyzed for ethyl benzene content (Table IV). Samples 2–8 (400 ml) were pooled and distilled through a vacuum-jacketed column (2.0×62 cm) packed with Heli-pak ™ metal packing. Fractions were analyzed by gas chromatography. The infrared spectrum of Sample #11 was identical to authenic ethyl benzene (Table V).

EXAMPLE 3

Reaction of Ethylene with Benzene using Reactor #1

The reactor was cycled in the usual manner, then filled with dry benzene at 94.5°. Ethylene and benzene were introduced at flow rates of 3 ml/min (47–50 psig, 1.05 mmoles/min) and 0.17 ml/min respectively. After steady-state conditions had been established, a total of 348 ml of the effluent was collected and fractionated by careful distillation through the Helipak column above; fractions were analyzed by gas chromatography (Table VI). The infrared spectra of Samples 6 and 8 were identical to those of authenic ethylbenzene and diethylbenzene (mixed isomers) respectively.

TABLE IV

Samples from Demonstration Run, Reaction of Ethylene with Benzene using Reactor #3. Benzene Flow 0.44 ml/min, T = 95° C.

| Sample | Ethylene Flow (ml/min) | P psig | Sample vol/ml | Ethylbenzene (% wt/vol) | Diethylbenzene(s) (% wt/vol) |
|---|---|---|---|---|---|
| 1 | 10 | 35 | 25 | 11.1 | 2.4 |
| 2 | 10 | 37 | 20 | 20.0 | 5.4 |
| 3 | 10 | 35 | 22 | 14.7 | 5.3 |
| 4 | 8 | 40 | 270 | 14.3 | 2.6 |
| 5 | 8 | 40 | 25 | 8.4 | 0.7 |
| 6 | 8 | 40 | 25 | 8.6 | 0.8 |
| 7 | 8 | 40 | 25 | 7.8 | 0.4 |
| 8 | 8 | 40 | 25 | Not observed | |

TABLE V

Distillate Fractions from the Preparative Run of Table IV. P = 730–733 mm, % Reported is Integration Ratio of Observed Peaks up to 240° on Gas Chromatographic Analysis of Neat Samples (0.15 μl)

| # | T Head (°C.) | T Pot °C. | Vol. or Wt. | Benzene % | Ethylbenzene % | Diethylbenzene % | Triethyl and Higher Benzene (%) |
|---|---|---|---|---|---|---|---|
| 1 | 78.5 | 84–85 | 35 ml | 100 | — | — | — |
| 2 | 78.5 | 85–86 | 66 ml | 100 | — | — | — |
| 3 | 78.5–78.8 | 86–87 | 85 ml | 100 | — | — | — |
| 4 | 78.5 | 87–97 | 85 ml | 100 | — | — | — |
| 5 | 78.8 | 97–137 | 55 ml | 100 | — | — | — |
| 6 | 78–126 | 137–141 | 6.0 g | 96 | 4.4 | — | — |
| 7 | 126–133 | 141 | 0.6 g | 27 | 73 | — | — |
| 8 | 133–134 | 141 | 0.2 g | 9.8 | 90 | — | — |
| 9 | 134 | 141 | 0.9 g | 15.7 | 84 | — | — |
| 10 | 134.5 | 141 | 0.4 g | 12.3 | 88 | — | — |
| 11 | 135 | 144–178 | 40.4 g | 0 | 100 | — | — |
| 12 | 135.5 | 178–202 | 6.9 g | 1.4 | 98.6 | — | — |
| 13 | 136–178 | 202–224 | 3.1 g | 0.5 | 41.2 | 58.3 | — |
| 14 | 178–180 | 224–249 | 1.6 g | — | 6.3 | 94.0 | — |
| 15 | Not Obs. | — | 0.7 g | — | 1.5 | 98.4 | — |
| 16 | Pot Residue | | 9.9 g | — | — | 56.5 | 43.5 |

TABLE VI

Distillate Fractions from Reaction of Benzene with Ethylene using Reactor #1. P = 730 mm, % is Ratio of Integrations for Peaks Observed in Gas Chromatographic Analysis up to 240°

| # | T Head °C. | T Pot °C. | Sample wt (g) | Benzene (%) | Ethylbenzene (%) | Diethylbenzene (%) | Triethyl and Higher (%) |
|---|---|---|---|---|---|---|---|
| 1 | 78.8 | 90 | 76.9 | — | — | — | — |
| 2 | 78.8 | — | 85.0 | 100 | — | — | — |
| 3 | 78.8 | 140 | 25.4 | 100 | — | — | — |
| 4 | 79–129 | 140–141 | 5.6 | 90.1 | 9.9 | — | — |
| 5 | 129–134 | 141–141.5 | 1.9 | 11.6 | 88.3 | — | — |
| 6 | 134 | — | 68.6 | — | 100 | — | — |
| 7 | 135–179 | — | 4.7 | 0.7 | 45.0 | 54.3 | — |
| 8 | 180–181 | to 305 | 13.8 | 0.2 | 0.75 | 99.2 | — |
| 9 | Pot Residue | — | 10.6 | — | 0.3 | 26.3 | (41.8 + 31.6) |

EXAMPLE 4

Monoalkylation of Benzene by Ethylene, Recycling Reactor Design (Reactor #4)

A bundle of Nafion TM "fibers" (<0.001" diam, 1200 E.W., 14.9 g) was pulled into the inner tube of a reflux condenser (1 cm I.D.×40 cm). The condenser was plugged at the bottom, filled with 70% nitric acid, and heated by circulating steam through the condenser jacket. The fiber bundle was then washed with distilled water and dried at 160° with a slow flow of dry nitrogen. The reactor was quickly assembled and 250 ml of dry benzene was placed in the pot. The outer jacket of the catalyst tube was evacuated to minimize heat loss. Reflux was established through the catalyst section; the reflux rate at the bottom of the catalyst tube was approximately 80 drops/min. Ethylene (0.15–0.26 mmoles/min) was introduced into the system; gas flow was observed in the exit bubbler. Samples of approximately 2 ml were periodically removed by syringe from the pot (Table VII).

The residual pot contents (170.5 g) were fractionated by distillation through a 50 cm×1 cm I.D. vacuum-jacketed vigreaux column equipped with a reflux ratio head; the resultant fractions were analyzed by gas chromatography (Table VIII). The conversion of ethylene recovered as ethylbenzene was about 17%.

TABLE VII

Samples from Reaction of Ethylene with Benzene in Recycling Reactor (Reactor #4)
T reaction = 78–79; Ethylene Flow 0.15–0.26 mmoles/min; Reflux Rate 80 Drops/min

| Sample | t (hrs) | Ethylbenzene (% w/v) | Diethylbenzene(s) (% wt/vol) |
|---|---|---|---|
| 1 | 0 | -0- | — |
| 2 | 1.5 | 0.03 | — |
| 3 | 9.0 | 0.58 | — |
| 4 | 22.5 | 1.50 | — |
| 5 | 29 | 2.26;2.32 | — |
| 6 | 32.5 | 2.86 | — |
| 7 | 43.5 | 3.91 | — |
| 8 | 50 | 4.64 | — |
| 9 | 68 | 6.95 | — |
| 10 | 74 | 7.82 | — |
| 11 | 90.5 | 10.9 | — |
| 12 | 102 | 11.6 | — |
| 13 | 115.5 | 13.2 | — |
| 14 | 126 | 14.5 | — |
| 15 | 144 | 18.1 | Trace |
| 16 | 169 | 24.1 | 0.37 |
| 17 | 236 | 30.0 | 0.45 |

TABLE VIII

Distillate Fractions from the Reaction of Table VII.
P = mm, % is Ratio of Integration on all Peaks Observed on Gas Chromatography of Neat Samples up to 240°

| Fraction | Wt (g) | T (°C.) | T pot | Benzene (%) | Ethylbenzene (%) | Diethyl- benzene (%) | Triethyl- benzene (%) |
|---|---|---|---|---|---|---|---|
| 1 | 73.0 | 79.2–80 | 89–110 | ~100 | Trace | — | — |
| 2 | 14.7 | 80–132 | 110–136 | 87 | 13 | — | — |
| 3 | 42.4 | 133–135.5 | 136–138 | Trace | 100 | — | — |
| 4 | 20.0 | 135.5 | 136.5–139 | — | 100 | — | — |
| Pot Residue | 3.4 | — | — | — | 58 | 38 | 4 |
| | 153.5 = 90.0% recovery | | | | | | |

$$\text{Total Ethylbenzene} = \frac{(0.13)(14.7 \text{ g}) + 42.4 \text{ g} + 20.02 \text{ g} + (.58)(3.4)}{170.5 \text{ g}}$$

= 39% w/w or 34% w/v

EXAMPLE 5

Reaction of Propylene with Benzene

Compared to ethylene, propylene reacted with benzene in the presence of Nafion ™ at much higher rates at lower temperatures. Indeed, immersion of the reactor in a water bath was necessary to maintain temperature control. Using Reactor #3, propylene flow was increased at several constant temperatures (Table IX). A preparative sample was taken after Sample 22 at conditions of: T=71°; benzene flow 0.56 ml/min; propylene flow 16 ml/min at 37 psig (3.3 mmoles/min) for the first 360 ml of effluent, then 20 ml/min at 37 psig (2.9 mmoles/min) for 105 ml of effluent (465 ml total).

At higher propylene flow rates, a considerable amount of a low-melting, waxy white solid, possibly propylene polymers was observed in the reactor effluent. As can be seen in Table IX, the principal effect of increased propylene flow was an increase in the extent of polyalkylation, with little or no increase in the amount of cumene produced.

The preparative sample (390.8 g) was slowly distilled through the vacuum-jacketed vigreaux column (50×1 cm) used previously; the samples were analyzed further by gas chromatography (Table X).

The reaction of propylene with benzene in the "recycling reactor" (Reactor #4) was also considerably more facile than the corresponding reaction with ethylene.

EXAMPLE 6

Reaction of Propylene with Benzene in "Recycling Reactor" to Produce Isopropylbenzene Nafion fiber (0.006″ diam. fibers, 18.1 g total) was packed loosely in small bundles in each of the bulbs of an 8-bulb Allihn condenser, then cleaned and dried in the usual manner; the fiber bundles shrank to approximately ⅓ their original volume during the drying process. The recycling reactor was assembled with 100 ml of dry benzene in the pot. Reflux was established through the catalyst reaction, then propylene was introduced at approximately 20 ml/min; no gas was observed in the outlet bubbler. The reactor was allowed to run for 22 hours to a final pot temperature of 118° (Sample 190 3). The contents of the pot were removed and replaced by 250 ml of fresh dry benzene. Reflux was again established and propylene flow resumed at 0.85 mmoles/min. Samples were removed periodically for analysis (Table XI). The residual pot contents at the end of 54 hours were fractionated by distillation through the vigreaux column used previously (Table XII).

TABLE IX

Reaction of Propylene with Benzene Using Reactor #3
Benzene Flow 0.56 ml/min

| # | T (°C.) | Propylene Flow ml/min | P psig | Propylene mmoles/min | Isopropyl- benzene % wt/vol | Diisopropyl- benzene(s) % wt/vol. | Triisopropyl- benzene(s) % wt/vol | Comments |
|---|---|---|---|---|---|---|---|---|
| 10 | 61 | 8 | 36 | 2.0 | 15.6 | 7.6 | 4.2 | All liquid |
| 12 | 61 | 12–13 | 40 | 2.8–3.0 | 17.4 | 12.4 | 11.4 | All liquid |
| 14 | 61 | 27–28 | 40 | 5.0–5.2 | 12.4 | 5.4 | 4.3 | Mostly gas in outlet |

TABLE IX-continued

Reaction of Propylene with Benzene Using Reactor #3
Benzene Flow 0.56 ml/min

| # | T (°C.) | Propylene Flow ml/min | P psig | Propylene mmoles/min | Isopropyl-benzene % wt/vol | Diisopropyl-benzene(s) % wt/vol. | Triisopropyl-benzene(s) % wt/vol | Comments |
|---|---|---|---|---|---|---|---|---|
| 18 | 71 | 10 | 32 | 2.4 | 18.4 | 9.4 | 2.4 | All liquid |
| 20 | 71 | 22 | 33 | 3.9 | 20.6 | 15.5 | 11.8 | All liquid |
| 22 | 71 | 37 | 32 | 5.6 | 19.3 | 17.3 | 15.8 | All liquid |
| 25 | 80 | 22 | 33 | 3.9 | 19.1 | 15.3 | 12.2 | All liquid |
| 27 | 80 | 42 | 33 | 6.2 | 18.9 | 17.9 | 19.2 | All liquid |
| 23 | 71 | 16–20 | 37 | 3.3–3.9 | 20.7 | 15.7 | 11.6 | Prep. Sample |

TABLE X

Distillates from Preparative Sample (#23) from Table IX
P = 730 mm

| # | T Head °C. | T Pot °C. | Wt. (g) | Benzene % | Isopropyl Benzene % | Diisopropyl Benzene(s) % | Triisopropyl Benzene(s) % | % Higher Alkylate |
|---|---|---|---|---|---|---|---|---|
| 1 | 80 | to 109 | 85.5 | 100 | — | — | — | — |
| 2 | 80–81 | 109–149 | 62.2 | 100 | — | — | — | — |
| 3 | 81–146 | 149–171 | 9.8 | 99 | 0.4 | — | — | — |
| 4 | 146–151 |  | 1.2 | 20 | 80 | — | — | — |
| 5 | 151–154 | 173–210 | 82.0 | — | 99.6 | 0.4 | — | — |
| 6 | 155–204 | 210–218 | 10.3 | — | 84 | 16 | — | — |
| 7 | 204–215 | 219–230 | 48.5 | — | 0.4 | 93 | 7 | — |
| 8 | 215–238 | 230–248 | 39.5 | — | — | 41 | 59 | — |
| 9 | 235–249 | 248–267 | 16.3 | — | — | — | 83 | 17 |
| 10 | 249→ | 267→ | 0.6 | — | — | — | 69 | 31 |
| Pot Residue |  |  | 7.2 | — | — | — | 17 | 83 |
|  |  |  | 363.1 | = 93% Recovery |  |  |  |  |

Total Isopropylbenzene = 91.5 g/370.8 g = 23% w/w, 20% w/v

It can readily be seen that the reactor design gives (as in the previous case) essentially monoalkylation as compared to the high proportion of polyalkylation observed in the reaction of propylene with benxene in the usual flow reactor.

TABLE XI

Reaction of Propylene with Benzene in the Recycling Reactor (Reactor #4)
Those marked % are ratios of integration on neat samples

| # | Time (hr) | Isopropylbenzene % wt/vol | Diisopropylbenzene(s) % wt/vol | Triisopropylbenzene(s) % wt/vol |
|---|---|---|---|---|
| 3 | (previous run) | 52.1 | 1.7 | — |
| 4 | -0- | 0.46 | — | — |
| 5 | 2.2 | 4.19 | 0.09 | — |
| 6 | 6.7 | 12.5 | 0.35 | 0.08 |
| 7 | 16.5 | 19.9 | 0.58 | 0.07 |
| 8 | 18.5 | 23.8 | 0.84 | 0.16 |
| 9 | 21 | 28.4 | 0.70 | — |
| 10 | 24 | 34.0 | 0.87 | — |
| 12 | 41.5 | 51.3 | 2.98 | — |
| 13 | 47 | 67.2 | 3.4 | 0.7 |
| 14 | 50 | 77% | — | — |
| 15 | 53 | 80.3% | 4.5 | — |
| 16 | (Pot 54 contents) | 76% | 4.8 | — |

0.85 mmoles/min ⟶ 2.75 moles

Total isopropyl groups recovered in product 1.74 moles or 63%

TABLE XII

Distillate Fractions from Distillation of Pot Contents from Reaction in Table XI.
P = 730 mm. % is Ratio of Integrations of Peaks on Gas Chromatographic Analysis to 240°

| # | T Head °C. | T Pot °C. | Wt (g) | Benzene % | Isopropyl-Benzene % | Diisopropyl-Benzene % | Triisopropyl-Benzene % |
|---|---|---|---|---|---|---|---|
| 1 | 80–82.5 | 124–136 | 16.7 | 100 | — | — | — |
| 2 | 82.5–151.5 | 136–154 | 16.5 | 98.3 | 1.7 | — | — |
| 3 | 151.5 | 154.5 | 73.5 | — | 100 | — | — |
| 4 | 151.5 | 155 | 102.5 | — | 100 | — | — |
| 5 | 151.5 | 155–197 | 10.7 | — | 100 | — | — |
| 6 | 152–243 | 197–260 | 14.0 | — | 19 | 79.6 | 1.0 |
| Pot Residue |  |  | 3.4 | — | 0.67 | 47.7 | 51.6 |

TABLE XII-continued

Distillate Fractions from Distillation of Pot Contents from Reaction in Table XI.
P = 730 mm. % is Ratio of Integrations of Peaks on Gas Chromatographic Analysis to 240°

| # | T Head °C. | T Pot °C. | Wt (g) | Benzene % | Isopropyl-Benzene % | Diisopropyl-Benzene % | Triisopropyl-Benzene % |
|---|---|---|---|---|---|---|---|
| | | | 237.31 = 90% recovery | | | | |

Benzene 12.5% w/w
Isopropylbenzene 72% w/w
Diisopropylbenzene(s) 5% w/w
Triisopropylbenzene(s) 0.7% w/w

EXAMPLE 7

Dealkylation of Diisopropylbenzene

A solution (10% w/v in dry benzene) of freshly distilled diisopropylbenzene (E.K., mixed isomers) was pumped through Reactor 190 1 at a flow rate of 0.28 ml/min. Check valves on the outlet maintained the reactor contents as liquid. Samples were taken at increasing temperatures and analyzed (Table XIII). At the highest temperature investigated (121°), the flow rate was increased to a maximum of 0.86 ml/min. The reactor was then allowed to stand overnight to obtain a sample which had been completely equilibrated 190 24 (Table XIV). It can readily be seen that equilibration of the mixture of isopropyl and diisopropylbenzene is essentially complete at temperatures greater than 110° at 0.28 ml/min, and up to about 0.7 ml/min at 120°; this corresponds to a total residence time in the catalyst region of about 20 min.

EXAMPLE 8

Dealkylation of Diethylbenzene

Dealkylation of diethylbenzene, as expected from the alkylation results, was somewhat less efficient (using the same reactor design) (Table XV).

TABLE XIII

Dealkylation of Diisopropylbenzene in the Presence of Excess Benzene Catalyzed by Nafion ® The Flow Rate of the 10% w/v Diisopropylbenzene in Benzene was 0.28 ml/min. Reactor #1

| # | T (°C.) | Isopropylbenzene, % wt/vol | Diisopropylbenzene(s) (% wt/vol) |
|---|---|---|---|
| 4 | 50 | 0.09 | 9.5 |
| 5 | 64 | 0.27 | 10.3 |
| 7 | 79 | 1.94 | 8.9 |
| 9 | 93 | 5.73 | 6.5 |
| 11 | 100 | 8.37 | 4.3 |
| 13 | 110 | 11.84 | 1.4 |
| 15 | 121 | 11.87 | 0.82 |

TABLE XIV

Conditions as in Table XIII; T = 121° C., Flow Rate as Indicated

| # | Flow Rate (ml/min) | Isopropylbenzene % wt/vol | Diisopropylbenzene % wt/vol |
|---|---|---|---|
| 15 | 0.28 | 11.87 | 0.82 |
| 17 | 0.39 | 12.00 | 1.23 |
| 19 | 0.56 | 10.84 | 1.2 |
| 22 | 0.86 | 10.57 | 2.7 |
| 24 | -0- | 10.25 | 0.44 |

TABLE XV

Dealkylation of Diethylbenzene (Koppers Co., Mixed Isomers, 5% wt/vol in Dry Benzene); the Flow Rate was 0.39 ml/min using Reactor #1

| # | T °C. | Ethylbenzene, % wt/vol | Diethylbenzene, % wt/vol |
|---|---|---|---|
| 5 | 70 | 0.22 | 4.52 |
| 8 | 90 | 0.57 | 4.16 |
| 10 | 104 | 0.50 | 4.38 |
| 12 | 120 | 1.00 | 4.03 |
| 14 | 140 | 2.03 | 3.30 |

EXAMPLE 9

Isomerization of Xylene

Reactor 190 1 was cycled in the usual manner and dried with nitrogen at 170°. Check valves of 10 psi and 25 psi cracking pressures were attached to the inlet and outlet (respectively) of the reactor. p-Xylene was introduced at 0.56 ml/min at 59°. Samples were taken at increasing temperatures, in every case allowing more than a reactor volume of p-xylene to pass through the reactor before taking a sample for analysis by gas chromatography. The results are presented in Table XVI. After the sample at 161° was taken, the reactor was allowed to stand at 161° for an additional 6 hours, then cooled to room temperature and allowed to stand two days; Sample 190 11 was taken on resumption of xylene flow at room temperature.

TABLE XVI

Isomerization of p-Xylene Catalyzed by Nafion ®
Reactor #1, Flow Rate 0.56 ml/min of p-xylene,
"%" is Integration Ratio

| # | T (°C.) | Toluene (%) | p-Xylene (%) | m-Xylene (%) | o-Xylene (%) |
|---|---|---|---|---|---|
| 2 | 59 | — | 100 | — | — |
| 4 | 79 | — | 100 | — | — |
| 6 | 100 | — | 100 | — | — |
| 8 | 139 | 3.3 | 91.3 | 5.3 | — |
| 10 | 161 | 2.6 | 85.7 | 11.7 | Trace |
| 11 | 161 - 6 hr | 11.7 | 57.3 | 24.8 | 6.2 |

What is claimed is:

1. A process for the alkylation of an organic compound, said organic compound being selected from the group consisting of mono and polynuclear aromatics, paraffins, organic acids and alcohols, which comprises the steps of
   (1) vaporizing said organic compound in a reflux zone
   (2) passing said vaporized organic compound through a catalyst zone to an overhead condenser whereby said vapor is condensed.
   (3) returning said condensed organic compound to said catalyst zone and in said catalyst zone contacting said condensed organic compound with said vaporized organic compound and an olefin in the presence of a solid acid catalyst at alkylating conditions whereby a mono-alkylate derivative of said organic compound is formed,
   (4) returning said mono-alkylate derivative and unreacted organic compound to said reflux zone, and
   (5) recovering said mono-alkylate derivative from said reflux zone.

2. The process of claim 1 including the steps of continuously adding fresh organic compound to said reflux zone of step (1).

3. The process of claim 1 wherein the solid acid catalyst is a fluorocarbon polymer containing pendant sulfonic acid groups.

* * * * *